United States Patent [19]
Uchiyama et al.

[11] Patent Number: 5,932,603
[45] Date of Patent: Aug. 3, 1999

[54] THROMBOLYTIC AGENTS

[75] Inventors: Hiroyuki Uchiyama, Chiba; Masahiro Iwaki, Ichikawa, both of Japan

[73] Assignee: Torii Pharmaceutical Co., Ltd., Tokyo, Japan

[21] Appl. No.: 08/849,864

[22] PCT Filed: Jan. 5, 1995

[86] PCT No.: PCT/JP95/00001

§ 371 Date: Jun. 13, 1997

§ 102(e) Date: Jun. 13, 1997

[87] PCT Pub. No.: WO96/20706

PCT Pub. Date: Jul. 11, 1996

[51] Int. Cl.$^6$ .................................................. A61K 31/415
[52] U.S. Cl. .......................................................... 514/392
[58] Field of Search ............................................... 514/392

[56] References Cited

U.S. PATENT DOCUMENTS 4,777,182 10/1988 Fujii et al. ............................... 514/392

FOREIGN PATENT DOCUMENTS

0190356 A1  6/1986  European Pat. Off. .

OTHER PUBLICATIONS

Ethical Drugs, Pharmaceutical Drugs in Japan, Aug. 1995, cover sheet and one–page description concerning the uses of the products(*) listed in the Oct. 1996 *Drugs in Japan; Ethical Drugs* publication.

*Drugs in Japan; Ethical Drugs*, published by Yakugyo Jiho Co., Ltd., Tokyo, Japan, Oct. 1996 Parts Only.

One–page translation of Table 2 in the 1994 *Journal of Japanese College of Angiology*.

*Journal of Japanese College of Angiology*, 1994, vol. 34, No. 6, including a one–page summary in English on p. 6 of the Journal.

*Primary Examiner*—Jerome D. Goldberg
*Attorney, Agent, or Firm*—Smith, Gambrell & Russell, LLP; Beveridge, DeGrandi, Weilacher & Young Intellectual Property Group

[57] ABSTRACT

The present invention relates to a thrombolytic agent capable of being orally administered, said agent comprising 6-amidino-2-naphthyl 4-[(4,5-dihydro-1H-imidazole-2-yl) amino]benzoate or a pharmaceutically acceptable acid addition salt thereof.

4 Claims, 3 Drawing Sheets

CHANGES IN THE AMOUNT OF PAI-1 ANTIGEN CAUSED BY THE COMPOUND OF THE PRESENT INVENTION

CHANGES IN THE AMOUNT OF PAI-1 ANTIGEN CAUSED BY THE COMPOUND OF THE PRESENT INVENTION

CHANGES IN THE AMOUNT OF PIC ANTIGEN IN THE HUMAN PLASMA CAUSED BY THE COMPOUND OF THE PRESENT INVENTION

THROMBOLYTIC AGENTS

DESCRIPTION

1. Technical Field

The present invention relates to a thrombolytic agent capable of being orally administered, said agent comprising 6-amidino-2-naphthyl 4-[(4,5-dihydro-1H-imidazole-2-yl)amino]benzoate or a pharmaceutically acceptable acid addition salt thereof.

2. Background Art

A clot formed by coagulation of blood in the heart or the blood vessel is called a thrombus, and a pathological process associated with the formation of said thrombus is called thrombosis. Thrombosis includes a variety of pathological states such as cerebral infarction, myocardial infarction, pulmonary infarctionm etc.

The formation of thrombus is originally a mechanism that serves to prevent the potential leakage of blood from the injured part of the blood vessel when it is injured for some reason. The formation of thrombus is closely associated with variation in blood components, abnormal blood circulation, and changes in properties of the walls of blood vessels. That is, when a blood vessel is injured for some reason, blood platelets adhere to the injured site and aggregate to form an aggregated mass in order to prevent bleeding therefrom. Furthermore, platelets, by aggregating to one another, release substances that activate coagulation factors present in the blood to promote thrombus formation leading to the formation of more rigid thrombi. There are a number of coagulation factors, which constitute the complex mechanism of activation in which the reaction proceeds in a cascade manner by one enzyme activating the next (the blood coagulation system). Also, some coagulation factors are directly activated by wounds or injured tissues, and the coagulation proceeds in a variety of ways. However, there are a lot of substances present in the blood that suppress the progress of coagulation, thereby suppressing the enhancement of abnormal coagulation. Blood clots are formed as needed but are lysed by the enzymes (the fibrinolytic enzymes) that dissolve clots in the blood when the hemostatic action becomes no longer needed and the blood vessel returns to the original state (the fibrinolytic system).

Thus, thrombus formation involves a variety of factors. However, the factors that are most directly involved in thrombus formation are platelets, coagulation factors, fibrinolytic factors and the like, and conventionally drugs affecting the above mentioned blood components have been developed and used for treatment of thrombosis that are caused by the presence of abnormal thrombi.

The methods of treatment of thrombosis are roughly divided into two groups by the mechanism of action: the anti-thrombotic therapy that prevents formation of thrombi, and the thrombolytic therapy that dissolves the formed thrombi.

The anti-thrombotic therapy has further been classified into two: the anti-platelet therapy and the anti-coagulation therapy.

The anti-platelet therapy is intended to suppress the functions of platelets involved in the early stages of thrombus formation and drugs such as classical aspirin and many other drugs that can be administered orally have been developed. They are now used to prevent recurrence of cerebral infarction, myocardial infarction, etc., to prevent occlusion after various bypass surgeries, to prevent restenosis after coronary angioplasty, and the like. Thus, they are used more as prophylactic drugs against thrombus formation than as therapeutic drugs. They have the problem of the presence of individual variation in appearance of efficacy, and of bleeding tendency because of the need for prolonged administration.

The anti-coagulation therapy is intended to inhibit thrombus formation by suppressing coagulation factors and is classified into the drugs for inhibiting activity of coagulation factors and the drugs for suppressing formation of coagulation factors. The former includes heparin, enzyme inhibitors, and the like. Since they are injections, they show anti-coagulation activity by intravenous administration. However, they have to be used under the supervision of a physician and also have the problem of bleeding tendencies and the like. The latter is a method that suppresses the formation of coagulation factors by antagonizing vitamin K which is required for production of coagulation factors in vivo and thereby for inhibiting the overall coagulation ability. The representative drug used is warfarin. Although warfarin can be administered orally and has been used for chronic diseases that require administration for a prolonged period time, it has a problem of strong bleeding tendencies as a side effect.

The method that treats thrombosis in a mechanism of action different from that of the anti-thrombotic therapy is the thrombolytic therapy. The purpose of the therapy is not suppression of the mechanism of thrombus formation but recanalization of blood circulation by dissolving the thrombus in the blood vessel and thereby removing the occlusion of the blood vessel.

Its mechanism of action is believed to activate plasminogen, a precursor of the fibrinolytic system-modulating factors, into plasmin, which plasmin dissolves thrombus by decomposing thrombus-forming fibrin in the blood vessel thus leading to recanalization of the occluded site. As the drugs used in the thrombolytic therapy there are known endogeneous substances such as tissue plasminogen activator (t-PA), urokinase (UK), etc. that are plasminogen activating factors which activate plasminogen into plasmin, microbially produced substances such as staphylokinase, streptokinase, etc., and recombinant formulation thereof. They are all injections and no such drugs for oral administration are known.

It is assumed that t-PA etc. are generally useful in intravenous administration. However, they have short half-lives and are quickly eliminated from the liver. In addition, since there may be inhibitors present in vivo, an administration in a large dosage is required for the thrombolytic activity to function at the site of clots. It has been reported that this transient administration of a large dose of a thrombolytic drug remarkably enhances systemic activity of thrombolysis, and thus canalization of the occluded site is expected on the one hand, whereas the formed plasmin decomposes fibrinogen and other coagulation factors, and injures the walls of the blood vessel thereby displaying bleeding symptoms on the other. Local administration of a thrombolytic drug against coronary thrombosis at myocardial infarction is indeed a very effective method of treatment, but insertion of a catheter into the blood vessel is a special technique and poses a great burden to the patient. Furthermore, it has been reported in the animal studies and clinical cases that although the administration of a thrombolytic agent temporarily canalizes the occluded site, reocclusion may easily occur.

For the above-mentioned reasons, it has been desired to develop a drug: that has an activity of dissolving thrombus, a direct cause of thrombosis, formed in the blood vessel; that does not show severe side effects such as bleeding, a problem associated with the conventional thrombolytic agents, and the like, and; that can be orally administered so that the burden on the patient may be alleviated.

DISCLOSURE OF THE INVENTION

As a result of intensive research in order to achieve the objective mentioned above, the present inventors have unexpectedly found that 6-amidino-2-naphthyl 4-[(4,5-dihydro-1H-imidazole-2-yl)amino]benzoate has an excellent thrombolytic activity and we have completed the present invention. Thus, the present invention relates to a thrombolytic agent capable of being orally administered, said agent comprising the above-mentioned compound of the present invention or a pharmaceutically acceptable acid addition salt thereof. The compound of the present invention is a known compound that is useful as an anti-trypsin agent, anti-plasmin agent, anti-kallikrein agent, anti-thrombin agent and anti-complement agent as set forth in Japanese Unexamined Patent Publication No. 61('86)-33173. However, as is evident from the pharmacological studies mentioned below, the activity of the compound of the present invention to dissolve thrombus by activating the fibrinolytic system was discovered for the first time by the present inventors, and the thrombolytic agent comprising the compound of the present invention and a pharmaceutically acceptable acid addition salt thereof is useful for diseases that are caused by thrombus. Thus, it can be used as a drug for treatment of venous thrombosis, myocardial infarction, pulmonary embolism, cerebral embolism, a slowly progressing cerebral thrombosis, and thrombotic embolism associated with vascular surgery and extracorporeal blood circulation, as well as for improvement of circulation disorders, improvement of various conditions associated with chronic atrial occlusion, for treatment of thrombosis and embolism associated with ischemic cerebrovascular disorders, and treatment of thrombosis and embolism in general.

FIELD OF INDUSTRIAL APPLICATION

As is evident from the pharmacological studies below which shows that the compound of the present invention dissolves thrombus by activating the fibrinolytic system, the compound of the present invention can be used as a drug for treatment of venous thrombosis, myocardial infarction, pulmonary embolism, cerebral embolism, a slowly progressing cerebral thrombosis, and thrombotic embolism associated with vascular surgery and extracorporeal blood circulation, as well as for improvement of circulation disorders, improvement of various conditions associated with chronic atrial occlusion, for treatment of thrombosis and embolism associated with ischemic cerebrovascular disorders, and treatment of thrombosis and embolism in general.

Various pharmacological studies are illustrated below for the compound of the present invention (6-amidino-2-naphthyl 4-[(4,5-dihydro-1H-imidazole-2-yl)amino]benzoate mesilate).

(1) Improvement effects on mortality of mouse pulmonary thrombosis lethal models In the experiment, ddY male mice that had been fasted for six hours were used. They were orally given 10 mg/kg of the compound of the present invention. Water was orally given to the control group. Six hours later, 10 units/mouse of thrombin was intravenously given into the caudal vein to induce thrombosis. Alive or death of the animal was assessed 16 hours after thrombin induction. The effect of improvement on mortality by the compound of the present invention was expressed in a survival rate. The results are shown Table 1.

TABLE 1

| Compound | Survival rate (%) |
| --- | --- |
| the compound of the present invention | 66.7 |
| water | 9.1 |

(2) Determination of the plasmin-like activity in the plasma using a synthetic substrate In the experiment, SD male rats that had been fasted overnight were used. They were orally given 30 mg/kg of the compound of the present invention. Subsequently the blood was serially collected as the sodium citrate-added blood from the descending aorta and then the blood was centrifuged to obtain plasma. Water was orally given to the control group and plasma was obtained in a similar manner.

The plasma obtained was incubated with 0.1 M borate buffer, pH 8.5, and 0.1 mM Boc-Val-Leu-Lys-MCA at 37° C. for 30 minutes. The reaction was stopped by adding 15% acetic acid and then the intensity of fluorescence was measured to determine the plasmin-like activity.

As a result, the group that was given the compound of the present invention has shown a marked enhancement in the plasmin-like activity as high as 0.968 nmol/min/ml as compared to 0.358 nmol/min/ml of the control group.

(3) Determination of the tissue plasminogen activator (t-PA)-like activity using a synthetic substrate The plasma obtained in the study example 2 mentioned above was incubated with 0.1 M borate buffer, pH 8.5, and 0.1 mM Phy-Gly-Arg-MCA at 37° C. for 30 minutes. The reaction was stopped by adding 15% acetic acid and then the intensity of fluorescence was measured to determine the t-PA-like activity.

As a result, the group that was given the compound of the present invention has shown a marked enhancement in the t-PA-like activity as high as 1.351 nmol/min/ml as compared to 0.648 nmol/min/ml of the control group.

(4) Determination of the amount of plasminogen activator inhibitor-1 (PAI-1) antigen in the plasma.

In the experiment, SD male rats that had been fasted overnight were used. They were orally given 30 mg/kg of the compound of the present invention. The blood was serially collected as the sodium citrate-added blood from the descending aorta and then the blood was centrifuged to obtain plasma.

One hundred $\mu$l of a solution of monoclonal antibody to PAI-1 in 10 mM carbonate buffer had been previously applied into a 96-well microtiter plate and the plate was left at 4° C. for 16 hours. After washing the plate four times with 10 mM phosphate buffer containing 0.1% Tween 20, the standard solution and the plasma samples were added. After leaving the plate at room temperature for two hours, washing was repeated four times again and 100 $\mu$l of the enzyme-labelled PAI-1 polyclonal antibody was added and the plate was incubated at room temperature for two hours. After washing four times to remove excess antibody, 100 $\mu$l of the citrate buffer containing 10 mg o-phenylenediamine and 0.1% hydrogen peroxide was added and was left at 30° C. for 30 minutes to develop the color. After stopping the reaction by adding 50 $\mu$l of 2 N sulfuric acid, absorbance at 405 nm was measured using the microplate reader to determine the amount of PAI-1 antigen in the plasma samples. The result is shown in FIG. 1.

In the control mechanism of thrombolysis, most of the t-PA released into the blood is quickly inhibited by its inhibitor, PAI-1, to lose its activity and, therefore, the decrease in the amount of PAI-1 results in the enhanced activity of thrombolysis. As shown in FIG. 1, the compound of the present invention evidently caused a decrease in the concentration of PAI-1, an inhibiting factor of fibrinolysis, in the blood.

(5) Determination of activated partial thromboplastin time (APTT)

To 100 μl of the reagent for determination of activated partial thromboplastin time (Platerin A-Auto) previously dissolved in distilled water, 100 μl of the plasma sample obtained in the above study example 4 was added, which was left at 37° C. for about three minutes. Then 100 μl of 0.25 M calcium chloride that had been prewarmed to 37° C. was added and the time elapsed to the formation of fibrin clots was determined by the coagulation meter (KC-10A, Amerung).

The result indicated no lengthening of APTT since the group that was given the compound of the present invention coagulated at 20.3 seconds as compared to 20.2 seconds of the control group.

Subsequently, a study on oral administration to the human was conducted.

(6) Determination of human activated partial thromboplastin time (APTT)

The compound of the present invention was orally given to the normal healthy individuals and blood was serially collected therefrom to obtain plasma.

To 100 μl of the reagent for determination of activated partial thromboplastin time (Platerin A-Auto) previously dissolved in distilled water, 100 μl of the plasma sample obtained as above was added, which was left at 37° C. for about three minutes. Then 100 μl of 0.25 M calcium chloride that had been prewarmed to 37° C. was added and the time elapsed to the formation of fibrin clots was determined by the coagulation meter (KC-10A, Amerung). The result indicated no lengthening of APTT since the group that was given the compound of the present invention coagulated at 18.4 seconds as compared to 18.5 seconds of the control group.

(7) Determination of the amount of human PAI-1 antigen

When the amount of PAI-1 antigen was measured in a similar manner to that in the study example 4 using the plasma obtained in the above study example 6, a marked decrease in the amount of PAI-1 antigen in the plasma was observed. The result is shown in FIG. 2.

(8) Determination of the amount of human PIC antigen

When the amount of plasmin-alpha$_2$-plasmin inhibitor complex (PIC) antigen was also determined using the in-vitro diagnostic "PIC Test" (distributed by Teijin) for the plasma obtained in the above study example 6, a positive increase in the amount of PIC was observed. The result is shown in FIG. 3.

In thrombolysis, the fibrinolytic reaction that is mediated by plasminogen activator (PA) and plasmin plays an important role. α$_2$-plasmin inhibitor (α$_2$-PI) is physiologically the most important inhibiting factor of plasmin and serves as a regulating factor in thrombolysis. Since little PIC occurs in the plasma of the normal individuals and is formed when plasmin is produced in vivo, the increased amount of PIC indicates enhancement of the systemic fibrinolytic system.

Thus, the compound of the present invention, when orally given, exhibits a very potent activity of thrombolysis.

Furthermore, in order to prove the effectiveness of the thrombolytic activity of the compound of the present invention, the potency of said compound and an anticoagulant, heparin, were compared using an experimental model in which thrombi had been previously formed in the blood vessel.

(9) A comparative test with the anticoagulant (heparin) in a rat thrombosis model A comparative test on potency of the compound of the present invention with an anticoagulant, heparin, was conducted by constricting the carotid arteries of the rat under anesthesia using the thrombosis model that produces thrombi at the constricted site (see Wessler Stanford, et al., J. Appl. Physiol. 14(6): 943–946 (1959)). This experimental model is the one used to demonstrate the effectiveness of t-PA and UK that have been used as thrombolytic agents.

In the experiment, SD male rats were used. The carotid veins of the rats were exposed under anesthesia and then ligated together with a wire of 2 mm in diameter. Five hundred units/ml of thrombin was injected into the blood vessel to produce a thrombin thrombus in the ligated vessel. Five minutes after the formation of the thrombus, the wire was removed and the open vessels were sutured. After the righting reflex was restored, 100 mg/kg of the compound of the present invention was orally given. The anticoagulant heparin was intravenously administered. Three hours after the administration of the drugs, the rats were sacrificed and the carotid vein that produced thrombus was extirpated. The residual thrombi in the extirpated blood vessel were counted based on the following scoring to evaluate the effectiveness of the drugs. The results are shown in Table 2.

Criterion:
Score 0 No thrombus
Score 1 Microthrombus
Score 2 Several small thrombotic masses
Score 3 Several large thrombotic masses
Score 4 Thrombotic masses that turned into cruors

TABLE 2

| Compound | Score |
|---|---|
| Compound of the present invention | 1 |
| Water | 4 |
| Heparin | 4 |

From the above result, it was demonstrated that the compound of the present invention is very effective against those thrombi on which anticoagulants have no effects.

It was also confirmed that the compound of the present invention, when orally given to the healthy individuals, does not induce any abnormalities in the subjective symptoms, the objective symptoms, or laboratory test results, and that it does not have any safety problems.

Figure 1:
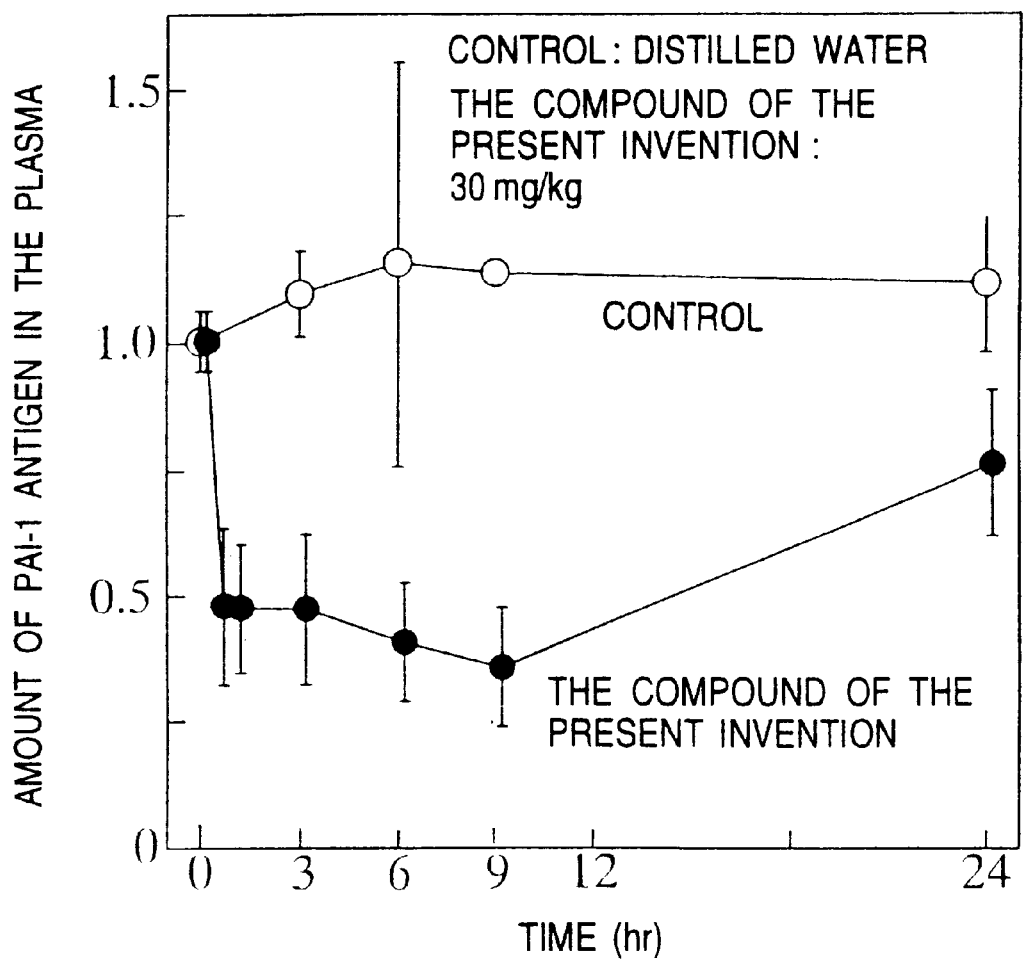
FIG. 1 shows changes in the amount of PAI-1 antigen in the blood of the rat after oral administration of the compound of the present invention. The horizontal axis denotes time (hours) after the administration, and the vertical axis denotes the ratio of the PAI-1 concentration in the blood relative to the value set at 1.0 of the concentration of PAI-1 in the blood immediately after the administration.
Figure 2:
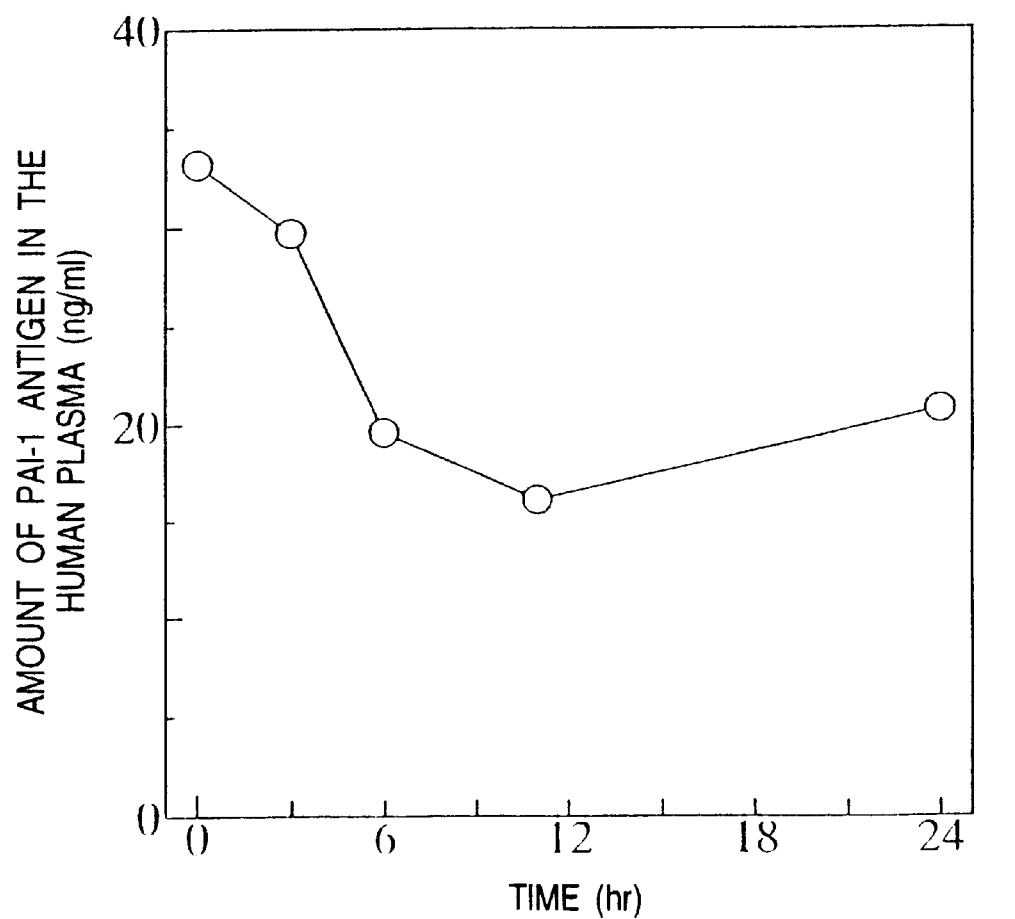
FIG. 2 shows changes in the amount of PAI-1 antigen in the blood of the human after oral administration of the compound of the present invention. The horizontal axis denotes time (hours) after the administration, and the vertical axis denotes the amount (ng/ml) of PAI-1 antigen in the blood.
Figure 3:
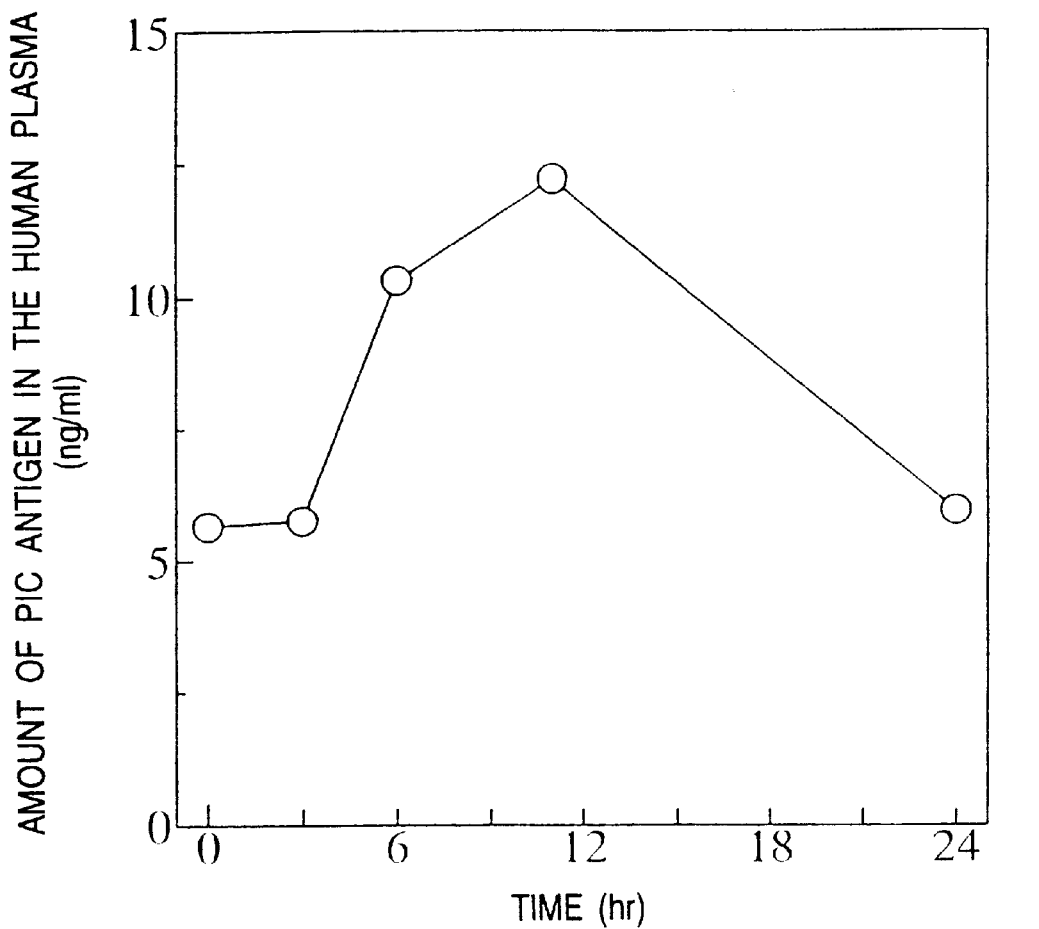
FIG. 3 shows changes in the amount of PIC antigen in the blood of the human after oral administration of the compound of the present invention. The horizontal axis denotes time (hours) after the administration, and the vertical axis denotes the amount (ng/ml) of PIC antigen in the blood.

The compound of the present invention may be generally administered in the form of pharmaceutical compositions. Examples of the above compositions include tablets, powders, capsules, syrups, or aqueous solutions. For compositions intended for oral administration, commonly used additives may be used such as excipients, lubricants, disintegrants, wetting agents, etc. The liquids intended for oral administration may be in the from of aqueous solutions, oleaginous solutions, solutions, emulsions, syrups, elixirs, etc., or they may be dispensed as dry syrups that are reconstituted with water or any other suitable solvent prior to use. The above-mentioned liquids may contain the common additives such as a suspending agent, a flavoring agent, a diluent, or an emulsifying agent. It may also be used as a suppository for rectal administration. The suppository may employ as the base any suitable materials such as cacao butter, lauric butter, macrogol, glycerogelatin, Witepsol, sodium stearate, or mixtures thereof, and, when desired, an emulsifying agent, a suspending agent, a preservative, and the like may be added.

BEST MODE FOR CARRYING OUT THE INVENTION

The compound of the present invention may be administered to mammals (including human patients) in the form of drugs for oral administration or for rectal administration. For the purpose of treating various diseases in the human caused by thrombus, the dosage is in the range of 100 to 1000 mg/day/person, preferably 200 to 800 mg/day/person, and more preferably 400 to 700 mg/day/person, but it can be adjusted as appropriate depending upon the severity of the disease, age and weight of the patient, etc.

We claim:

1. A method for producing thrombolysis in an animal comprising:

administering to an animal in need thereof, an effective amount of 6-amidino-2-napthyl 4-[(4,5-dihydro-1H-imidazole-2-yl)amino]-benzoate or a pharmaceutically suitable, salt thereof sufficient to produce thrombolysis.

2. A method for producing thrombolysis in an animal comprising:

administering to an animal in need thereof, an effective amount of a composition comprising 6-amidino-2-napthyl 4-[(4,5-dihydro-1H-imidazole-2-yl)amino]-benzoate or a pharmaceutically suitable salt thereof and a pharmaceutically acceptable carrier sufficient to produce thrombolysis.

3. A method for the treatment of myocardial infarction comprising:

administering to an animal in need thereof, an effective amount of 6-amidino-2-napthyl 4-[(4,5-dihydro-1H-imidazole-2-yl)amino]-benzoate or a pharmaceutically suitable salt thereof sufficient to produce thrombolysis.

4. A method for the treatment of myocardial infarction comprising:

administering to an animal in need thereof, an effective amount of a composition comprising 6-amidino-2-napthyl 4-[(4,5-dihydro-1H-imidazole-2-yl)amino]-benzoate or a pharmaceutically suitable salt thereof and a pharmaceutically acceptable carrier sufficient to produce thrombolysis.

* * * * *